(12) United States Patent
Gunzburg et al.

(10) Patent No.: US 6,821,776 B1
(45) Date of Patent: Nov. 23, 2004

(54) RECONSTITUTING RETROVIRAL VECTOR (RECON VECTOR) FOR TARGETED GENE EXPRESSION

(75) Inventors: Walter Gunzburg, Molding (AT); Dieter Klein, Tulln (AT); Walter Tabotta, Vienna (AU); Brian Salmons, Markt Inderstdorf/Ainhofen (DE)

(73) Assignees: Institut fur Virologie Teilrechtsfahiges; Institut an der Veterinarmedizinischen Universitat Wien, Vienna (AT)

(*) Notice: Subject to any disclaimer, the term of this patent is extended or adjusted under 35 U.S.C. 154(b) by 68 days.

(21) Appl. No.: 09/610,215

(22) Filed: Jul. 5, 2000

Related U.S. Application Data

(63) Continuation of application No. PCT/EP99/00002, filed on Jan. 3, 1999.

(30) Foreign Application Priority Data

Jan. 6, 1998 (DK) ............................................. 0005/98

(51) Int. Cl.$^7$ ............................................. C12N 15/867
(52) U.S. Cl. ................... 435/320.1; 435/325; 435/455; 435/456; 435/457; 514/44; 536/23.1; 536/24.1
(58) Field of Search .............................. 435/320.1, 325, 435/455, 456, 457; 514/44; 536/23.1, 24.1

(56) References Cited

U.S. PATENT DOCUMENTS 5,658,775 A  8/1997  Gilboa ......................... 435/56

FOREIGN PATENT DOCUMENTS

| WO | WO 89/11539 | 11/1989 |
| WO | WO 96/07748 A1 | 3/1996 |
| WO | WO 96/28563 | 9/1996 |
| WO | WO 97/09440 | 3/1997 |

OTHER PUBLICATIONS

Anderson Nature 392(Supplement):25–30 1998.*
Palu et al. Journal of Biotechnology 68:1–13 1999.*
Verma et al. Nature 389:239–242 1997.*
Alexander et al. Biotechniques 23: 64–66, Jul. 1997.*
Anderson, W.F. Human Gene Therapy. Apr. 30, 1998. Nature 392: 25–30.*
Kmiec, E.B. Gene Therapy May–Jun. 1999. American Scientist 87: 240–247.*
Walter H. Günzburg (2001) "Editorial overview. The importance of being RCR", Current Opinion in Molecular Therapeutics 3(5): 437–438.
Tabotta et al. (2001) "Genetic reshuffling reconstitutes functional expression cassettes in retroviral vectors", J. Gene Med 3; 418–426.
Karavanas et al. (1998) "Cell targeting by murine retroviral vectors", Critical Reviews in Oncology/Hematology 28: 7–30.
Walter H. Günzburg et al. (1996) "Retroviral vector targeting for gene therapy", Cytokines and Molecular Therapy 2: 177–184.
Walter H. Günzburg et al. (1996) "Development of retroviral vectors a safe, targeted gene delivery systems", J. Mol. Med 74:171–182.

* cited by examiner

Primary Examiner—David A. Lambertson
(74) Attorney, Agent, or Firm—Baker Botts LLP

(57) ABSTRACT

The present invention relates to a retroviral vector which is especially applicable as a safe gene transfer vehicle for targeted gene therapy. Said retroviral vector comprises one or more promoters inserted in antisense orientation within the 5' LTR region and one or more coding sequences inserted in antisense orientation within the 3' LTR region. Both, the promoter as well as the coding sequence, are additionally inserted in such a way as to ensure that the promoter and the coding sequence become duplicated during the process of reverse transcription in a target cell and thus appear in the 3' as well as in the 5' LTR region of the resulting provirus in a fashion where the promoter is located upstream of the coding sequence allowing it to drive gene expression. This system avoids any leakiness of gene expression in the packaging cells, and allows expression of transferred genes in the target cell without the necessity for external stimuli.

16 Claims, 1 Drawing Sheet

ReCon Vector
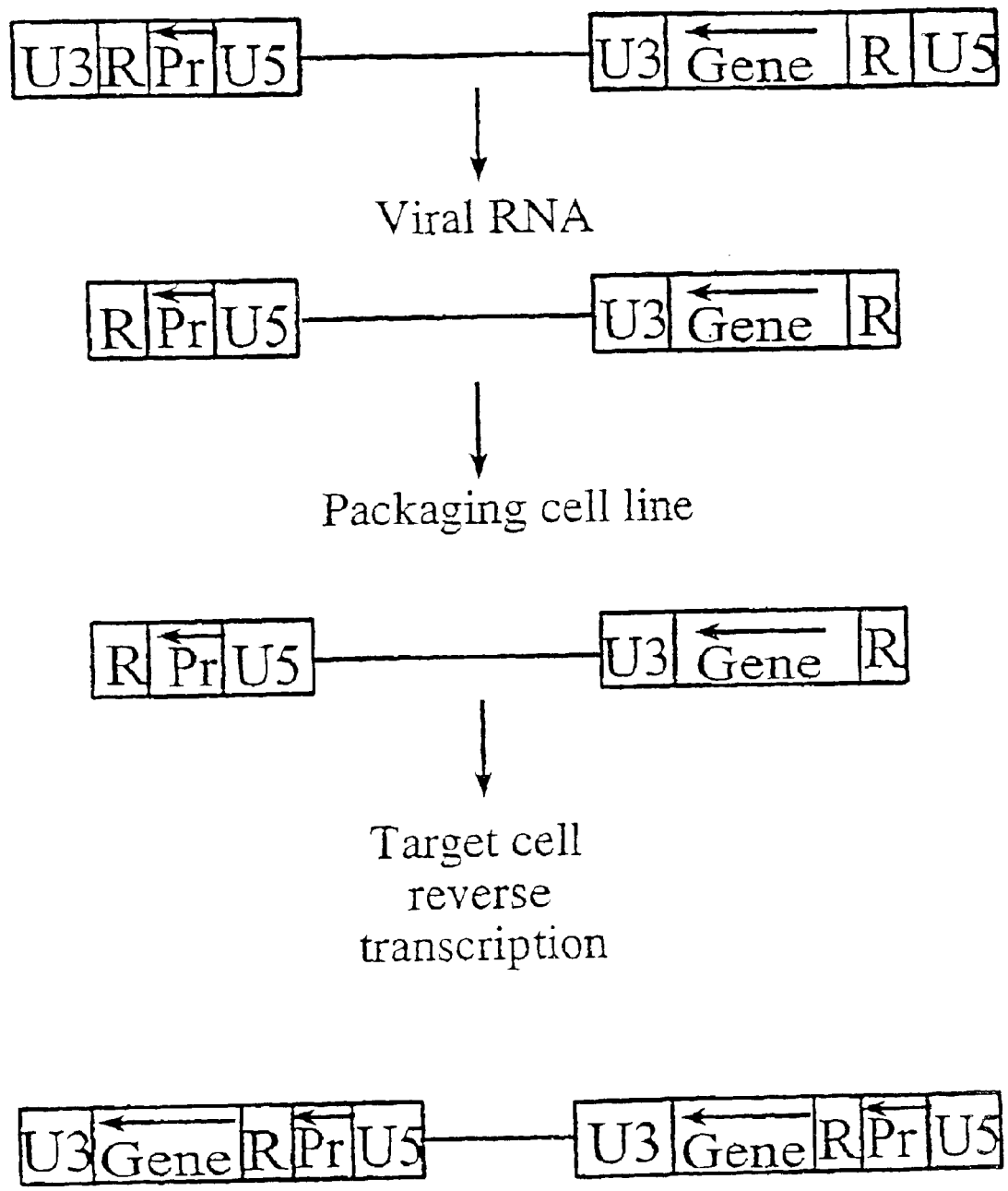

RECONSTITUTING RETROVIRAL VECTOR (RECON VECTOR) FOR TARGETED GENE EXPRESSION

RELATED APPLICATION(S)

This application is a continuation of PCT/EP99/00002 filed Jan. 3, 1999 and published in English on Jul. 15, 1999, which claims priority to DK 0005/98 filed Jan. 6, 1998. The entire teachings of PCT/EP99/00002 and DK 0005/98 are incorporated herein by reference.

BACKGROUND OF THE INVENTION

The most efficient and well developed systems for in vivo gene therapy are based upon retroviruses because the use of retroviral vectors (RV) is currently the method of choice for the transfer of therapeutic genes in a variety of approved protocols both in the USA and in Europe (Kotani, H., et. al., Human Gene Therapy 5: 19–28(1994)). Retroviruses infect a wide variety of cells and are ideal tools for the stable delivery of genes to cells since the retrovirus is able to integrate the DNA form of its genome into the genome of the target cell. Thus, all daughter cells of an infected cell carry the retroviral vector DNA including the therapeutic gene. However, current efficient transfer of therapeutic genes usually requires that the infection of target cells with the RV carrying the genes occurs in vitro, and successfully infected cells are then returned to the affected individual (Rosenberg, S. A., et. al., Hum. Gene Ther. 3:75–90(1992); Anderson, W. F., Science 256:808–813(1992)). Such ex vivo gene therapy protocols are ideal for correction of medical conditions in which the target cell population can be easily isolated. Additionally, the ex vivo infection of target cells allows the administration of large quantities of concentrated virus which can be rigorously safety tested before use.

Unfortunately, only a fraction of the possible applications for gene therapy involve target cells that can be easily isolated, cultured and then reintroduced. Additionally, the complex technology and associated high costs of ex vivo gene therapy effectively preclude its disseminated use world-wide. Future facile and cost-effective gene therapy will require an in vivo approach in which the RV, or cells producing the recombinant virus, are directly administered to the patient in the form of an injection or simple implantation of RV producing cells.

This kind of in vivo approach, of course, introduces a variety of new problems. First of all, and above all, safety considerations have to be addressed. Virus will be produced, possibly from an implantation of virus producing cells, and there will be no opportunity to precheck the produced virus. It is important to be aware of the finite risk involved in the use of such systems.

To minimize this risk the so-called ProCon vector has been developed as a safe gene transfer vehicle for targeted gene therapy using the principle of promoter conversion typical for retroviruses (PCT/EP95/03445):

The retroviral genome consists of an RNA molecule with the structure R-U5-gag-pol-env-U3-R. During the process of reverse transcription, the U5 region is duplicated at the right hand end of the generated DNA molecule, whilst the U3 region is duplicated and placed at the left hand end of the generated DNA molecule. The resulting structure U3-R-U5 is called LTR (Long Terminal Repeat) and is thus identical and repeated at both ends of the DNA structure or provirus. The U3 region at the left hand end of the provirus harbours the promoter. This promoter drives the synthesis of an RNA transcript initiating at the boundary between the left hand U3 and R regions and terminating at the boundary between the right hand R and U5 region. This RNA is packaged into retroviral particles and transported into the target cell to be infected. In the target cell the RNA genome is again reverse transcribed as described above.

In the ProCon vector the right hand U3 region is altered, but the normal left hand U3 structure is maintained; the vector can be normally transcribed into RNA utilizing the normal retroviral promoter located within the left hand U3 region. However, the generated RNA will only contain the altered right hand U3 structure. In the infected target cell, after reverse transcription, this altered U3 structure will be placed at both ends of the retroviral structure.

The altered region carries a polylinker instead of the U3 region. Thus, any promoter, including those directing tissue specific expression can be easily inserted. This promoter is then utilized exclusively in the target cell for expression of linked genes carried by the retroviral vector. Accordingly, in the packaging cell line the expression of the retroviral vector is regulated by the normal unselective retroviral promoter contained in the U3 region. However, as soon as the vector enters the target cell promoter conversion occurs, and the therapeutic and/or marker genes are expressed from a tissue specific promoter of choice introduced into the polylinker. Not only can virtually any tissue specific promoter be included in the system, providing for the selective targeting of a wide variety of different cell types, but additionally, following the conversion event, the structure and properties of the retroviral vector no longer resemble that of a virus. This, of course, has extremely important consequences from a safety point of view, since other retroviral vectors readily undergo genetic recombination with the retroviral packaging construct and/or endogenous retroviruses to produce potentially pathogenic viruses. Promoter conversion vectors do not resemble retroviruses because they no longer carry U3 retroviral promoters after conversion thus reducing the possibility of genetic recombination.

Rather than a tissue specific promoter a regulatable promoter can be inserted in the polylinker, allowing the conditional expression of genes carried by the retroviral vector.

However, all current systems of controlling gene expression are not absolute, and all require the additional inconvenience of requiring the presence of an inducer or repressor substance or stimulus.

SUMMARY OF THE INVENTION

The invention comprises the following, alone or in combination:

A retroviral vector comprising one or more promoters inserted in antisense orientation within the 5' LTR region and one or more coding sequences inserted in antisense orientation within the 3' LTR region, both, the promoter as well as the coding sequence, inserted in such a way as to ensure that the promoter and the coding sequence become duplicated during the process of reverse transcription in a target cell and appear in the 3' as well as in the 5' LTR region of the resulting provirus in a fashion where the promoter is located upstream of the coding sequence allowing it to drive gene expression.

the retroviral vector as above, wherein said promoter is inserted within the U5 region of the 5' LTR;

the retroviral vector as above, wherein said coding sequence is inserted within the U3 region of the 3' LTR;

the retroviral vector as above, wherein said coding sequence comprises heterologous DNA;

the retroviral vector as above, wherein said coding sequence is selected from one or more elements of the group consisting of marker genes, therapeutic genes, antiviral genes, antitumour genes, cytokine genes and/or toxin genes;

the retroviral vector as above, wherein said promoter is a strong, constitutive promoter;

the retroviral vector as above, wherein said retroviral vector is replication-defective;

the retroviral vector as above, wherein said retroviral vector is based on a vector of the pLXSN family;

the retroviral vector as above, wherein said retroviral vector is based on a promoter conversion vector;

a recombinant retroviral vector system comprising a retroviral vector as above as a first component, and a packaging cell line harbouring at least one retroviral and/or recombinant retroviral construct coding for proteins required for said retroviral vector to be packaged;

a retroviral particle produced by transfecting a packaging cell line of a retroviral vector system as above with the retroviral vector as above;

a retroviral provirus produced by infection of target cells with a recombinant retroviral particle as above;

mRNA of a retroviral provirus as above;

RNA of a retroviral vector as above;

a host cell infected with a retroviral particle as above;

a pharmaceutical composition containing a therapeutically effective amount of a recombinant retroviral particle as above and/or a recombinant retroviral vector system as above;

a method for introducing homologous and/or heterologous nucleotide sequences into target cells comprising infecting the target cells with recombinant retroviral particles as above;

use of a recombinant retroviral vector as above and/or of a recombinant retroviral vector system as above and/or of a retroviral particle as above for producing a pharmaceutical composition for gene therapy.

BRIEF DESCRIPTION OF THE DRAWINGS

The FIGURE is a schematic representation of the ReCon Vector.

DETAILED DESCRIPTION OF THE INVENTION

The present invention relates to a new retroviral vector which is especially applicable as a safe gene transfer vehicle for targeted gene therapy. The new vector enables the expression of, e.g., toxic genes, the expression of genes with a specific function that is incompatible with virus vector production and the expression of genes causing vector rearrangements necessary for specific biochemical operations.

It is an object of the present invention to further improve retroviral vectors for gene transfer into target cells, especially to provide a system which avoids any leakiness of gene expression in the packaging cells and which allows expression of transferred genes only in the target cell, preferably without necessity for external regulator substances or stimuli.

To achieve the foregoing and other objects, the present invention provides a retroviral vector comprising one or more promoters inserted in antisense orientation within the 5' LTR region and one or more coding sequences inserted in antisense orientation within the 3' LTR region, both, the promoter as well as the coding sequence, inserted in such a way as to ensure that the promoter and the coding sequence become duplicated during the process of reverse transcription in a target cell and appear in the 3' as well as in the 5' LTR region of the resulting provirus in a fashion where the promoter is located upstream of the coding sequence allowing it to drive gene expression (see the FIGURE).

First of all, in the antisense orientation there is no gene following on the left (downstream) of the promoter. Additionally, the gene to be transferred and expressed in the target cell is non-functional because there is no promoter located to the right (upstream) of it.

To generate the retroviral particle and the packaged vector, respectively, the principle of a retroviral vector system is used. This system consists of two components: the retroviral vector itself in which the genes encoding the viral proteins have been replaced, and a packaging cell line which provides the modified retrovirus with the missing viral proteins. This packaging cell line has been transfected with one or more plasmids carrying the genes enabling the modified retroviral vector to be packaged, but lacks the ability to produce replication competent viruses.

After introduction of the vector into the packaging cell line, the retroviral vector is transcribed into RNA. This transcription is regulated by the normal unselective retroviral promoter contained in the U3 region of the 5' LTR (see above) and initiates at the boundary between the U3 and R region and terminates at the boundary between the R and U5 region of the 3' LTR. The RNA which represents the recombinant retroviral genome is packaged by the viral proteins produced by the packaging cell line to form retroviral particles which bud from the cell. These are used to infect the target cell.

After infection of the target cell, the recombinant viral RNA will be reverse transcribed into DNA. During this process the promoter inserted in antisense orientation at the 5' end of the viral RNA will be duplicated and translocated to the 3' end of the generated DNA molecule, whilst the coding sequence(s) from the 3' end of the viral RNA will be duplicated and translocated to the 5' end of the DNA molecule (see the FIGURE).

As a result of this process the promoter and the gene are present twice within the target cells. Further, each copy of the gene is now linked to a copy of the promoter located upstream relative to the coding region allowing the gene to be expressed in the target cell. Consequently, this system avoids any leakiness of gene expression in the packaging cells, and allows expression of transferred genes in the target cell without the necessity for external stimuli.

In a preferred embodiment of the invention the promoter is inserted within the U5 region of the 5' LTR, preferably wholly or partly replacing the U5 region. Nevertheless, the promoter can also be inserted between the R and U5 region of the 5'LTR.

The gene coding sequences are especially inserted within the U3 region of the 3' LTR, preferably wholly or partly replacing the U3 region. Alternatively, they can be inserted between the R and U3 region of the 3' LTR.

In a further preferred embodiment the coding sequences comprise heterologous DNA. The term "heterologous" is used for any combination of DNA sequences that is not normally found intimately associated in nature.

The coding sequences are preferably, but not limited to one or more elements of the group consisting of marker genes, therapeutic genes, antiviral genes, antitumour genes, cytokine genes and/or toxin genes.

Said marker and therapeutic genes are preferably selected from one or more elements of the group consisting of β-galactosidase gene, neomycin gene, Herpes Simplex Virus thymidine kinase gene, puromycin gene, cytosine deaminase gene, hygromycin gene, secreted alkaline phosphatase gene, guanine phosphoribosyl transferase (gpt) gene, alcohol dehydrogenase gene, hypoxanthine phosphoribosyl transferase (HPRT) gene, green fluorescent protein (gfp) gene, cytochrome P450 gene and/or toxin genes such as a subunit of diptheria, pertussis toxin, tetanus toxoid.

Additionally, the retroviral vector may comprise one or more elements regulating expression of the coding sequences.

The inserted promoter is preferably a strong, constitutive promoter such as that of cytomegalovirus, simian virus 40, Rous Sarcoma Virus, or the ubiquitin C promoter, or in another embodiment a promoter that controls target cell specific expression and may be regulatable by transacting molecules.

The target cell specific regulatory elements and promoters are preferably, but not limited to one or more elements of the group consisting of Whey Acidic Protein (WAP), Mouse Mammary Tumour Virus (MMTV), β-lactoglobulin and casein specific regulatory elements and promoters, which may be used to target human mammary tumours, pancreas specific regulatory elements and promoters including carbonic anhydrase II and β-glucokinase regulatory elements and promoters, lymphocyte specific regulatory elements and promoters including human immunodeficiency virus (HIV), immunoglobulin and MMTV lymphocytic specific regulatory elements and promoters and MMTV specific regulatory elements and promoters such as $^{MMTV}$P2 conferring responsiveness to glucocorticoid hormones or directing expression to the mammary gland, T-cell specific regulatory elements and promoters such as T-cell receptor gene and CD4 receptor promoter, B-cell specific regulatory elements and promoters such as immunoglobulin promoter or mb1. Said regulatory elements and promoters regulate preferably the expression of at least one of the coding sequences of said retroviral vector.

Furthermore, the retroviral vector is especially replication-defective and preferably based on a vector of the pLXSN family and/or on a promoter conversion vector (see above).

The LTR regions are preferably, but not limited, selected from at least one element of the group consisting of LTR's of Murine Leukaemia Virus (MLV), Mouse Mammary Tumour Virus (MMTV), Murine Sarcoma Virus (MSV), Simian Immunodeficiency Virus (SIV), Human Immunodeficiency Virus (HIV), Human T-cell Leukaemia Virus (HTLV), Feline Immunodeficiency Virus (FIV), Feline Leukaemia Virus (FELV), Bovine Leukaemia Virus (BLV) and Mason-Pfizer-Monkey Virus (MPMV).

In a further embodiment of the invention a retroviral vector system is provided comprising a retroviral vector as described above as a first component and a packaging cell line harbouring at least one retroviral and/or recombinant retroviral construct coding for proteins required for said retroviral vector to be packaged.

The packaging cell line harbours retroviral or recombinant retroviral constructs coding for those retroviral proteins which are not encoded in said retroviral vector. The packaging cell line is preferably, but not limited, selected from an element of the group consisting of psi-2, psi-Crypt, psi-AM, GP+E-86, PA317, GP+envAM-12, Fly A13, BOSC 23, BING, Fly RD 18, ProPak-X, -A.52 and -A.6, or of any of these supertransfected with recombinant constructs allowing expression of surface proteins from other enveloped viruses.

After introducing the retroviral vector of the invention as described above in a retroviral packaging cell line a retroviral particle is provided comprising the recombinant retroviral genome.

The invention includes also a retroviral provirus, mRNA of a retroviral provirus according to the invention, any RNA resulting from a retroviral vector according to the invention and cDNA thereof, as well as host cells infected with a retroviral particle according to the invention.

A further embodiment of the invention provides a method for introducing homologous and/or heterologous nucleotide sequences into target cells (as e.g. CRFK, NIH/3T3, T-47D, RAT2, MV 1 LU (NBL-7), T-24, PG13, PA317, A20, HT-1080, PANC-1, MIA PA CA-2, HEP G2, 293, MCF-7, CV-1, COS 1, COS 7, FLY2A1) comprising infecting a target cell population in vivo and in vitro with recombinant retroviral particles produced by the packaging cell line. The nucleotide sequences are selected from one or more elements of the group consisting of genes or parts of genes encoding for proteins, regulatory sequences and promoters.

The retroviral vector, the retroviral vector system and the retroviral provirus as well as RNA thereof is used for producing a pharmaceutical composition for in vivo and in vitro gene therapy in mammals including humans. Furthermore, they are used for targeted integration in homologous cellular sequences.

EXAMPLES

The following examples will further illustrate the present invention. It will be well understood by a person skilled in the art that the provided examples in no way may be interpreted in a way that limits the applicability of the technology provided by the present invention to these examples.

1. Construction of a ProCon Based Expression Vector with an Elongated Packaging Signal The ProCon based expression vector (see PCT Application No. PCT/EP95/03445) pLX125 was constructed by ligation of the fragment containing the MLV-5' LTR as well as the elongated packaging signal of pLXSN (Miller and Rosman (1989) Biotechniques 7: 980–990) with the fragment containing the neomycine gene under the control of the SV40 promoter and the MMTV-3' LTR of a vector designated p125.6 (see also PCT Application No. PCT/EP95/03445).

The vector pLXSN was digested with the restriction enzymes AflIII and BamHI resulting in a 3545 hp fragment, and p125.6 was digested with the restriction enzymes AflII and BamHI resulting in a 4263 bp fragment. The DNA fragments of both digests were purified by running on a 0.8% agarose gel, the DNA bands were excised and DNA eluted using the Qiaquick protocol (Qiagen). After ethanol precipitation the DNA fragments were resuspended in water.

40 ng of the 3545 bp AflIII/BamHI fragment from vector pLXSN and 100 ng of the 4263 bp AflIII/BamHI fragment from vector p125.6 were mixed and ligated at room temperature for 1 h using T4 ligase (Boehringer). Nucleotides were filled in using the Klenow enzyme for 12 h at 12° C. followed by a ligation of the blunt ends at 14° C. for 14 h using the T4 ligase (Boehringer). The enzymes were inactivated at 65° C. for 20 min. The DNA was butanol precipitated with a 10 fold volume of butanol and resuspended in water and electroporated into DH10B bacteria (Gibco). Ampicillin resistant colonies were selected, DNA prepared and test digested with the restriction enzymes EcoRI, AflII, StuI, BssHII and KpnI. The final correct ProCon vector was designated pLX125.

II. Construction of the ProCon Based Expression Vector pLXPCMTV

The ProCon expression vector pLXPCMTV—containing only one single SacII restriction site—was constructed by removing the SacII restriction site upstream the 5' LTR in the expression vector pLX125 by partial restriction digest. pLX125 was partially digested with the restriction enzyme SacII and heat inactivated for 20 min at 65° C. For blunt end ligation the nucleotide ends were cut off with T4 polymerase (New England BioLabs) for 20 min at 12° C. The DNA was purified by running on a 0.8% agarose gel, the 7810 bp fragment DNA band was excised and DNA eluted using the Qiaquick protocol (Qiagen). After ethanol precipitation the DNA was resuspended in water. 10 ng of the DNA fragment was ligated for 12 h at 4° C. using T4-ligase (Boehringer). The ligase was inactivated at 65° C. for 20 min and the DNA butanol precipitated with a 10 fold volume of butanol. The precipitated DNA was resuspended in water and electroporated into DH10B bacteria (Gibco). Ampicillin resistant colonies were selected, DNA prepared and test digested with the restriction enzymes MluI and SacII and sequenced. The final correct plasmid was designated pLXPCMTV.

III. Construction of an egfp Expressing ProCon Vector

As a control vector for the ReCon system the ProCon expression vector pLXPCEGFP (=pLESNm1P) was constructed by ligation of the fragment containing the egfp gene obtained from plasmid pEGFP-1 (Clontech) with the pLXPCMTV backbone.

The pLXPCMTV backbone was digested with the restriction enzyme HpaI yielding a 7800 bp fragment. For isolation of the egfp gene the plasmid pEGFP was digested with the restriction enzymes HpaI and SmaI yielding a 860 bp fragment. The digestion mixtures were purified on a 0.8% agarose gel. The 7800 bp and the 860 bp fragment were excised and the DNA eluted using the Qiaex protocol (Qiagen).

40 ng of the pLXPCMTV backbone and 50 ng of the HpaI/SmaI fragment were mixed and ligated for 14 hours at 16° C. using T4 ligase (Promega). The ligase was inactivated at 65° C. for 20 min and the DNA butanol precipitated with 10 fold volume of butanol. The precipitated DNA was resuspended in water and electroporated into DH10B bacteria (Gibco). Ampicillin resistant colonies were selected, DNA prepared and test digested with the restriction enzymes KpnI, SpeI or BamHI/XhoI and sequenced. The final correct plasmid was designated pLXPCEGFP (=pLESNm1P).

IV. Construction of an Expression Vector Containing the Inverse egfp Gene Within the 3'LTR Region.

The expression vector pLXPCEGFP.r was constructed by ligation of the fragment containing the egfp gene obtained from plasmid pEGFP-1 (Clontech) with the ProCon based pLXPCMTV backbone as described above (see item II).

The pLXPCMTV backbone was digested with the restriction enzymes MluI and SacII yielding a 6599 bp fragment with the eliminated MMTV U3 region.

The egfp.pA gene including the polyA site was isolated from the plasmid pEGFP-1 using the PCR method. The left hand primer (5'-ATAGTA<u>ACGCGT</u>GGTCGCCACCATGGTGAG-3') (SEQ ID NO:1) was specific to the beginning of the egfp gene also creating a new MluI restriction site (underlined), and the right hand primer (5'-GCGAT<u>CCGCGG</u>TGGACAAACCACAACTAGA-3') (SEQ ID NO:2) was specific to the end of the egfp gene also creating a new SacII restriction site (underlined). PCR resulted in a 978 bp fragment. The fragment was purified by running on a 0.8% agarose gel, the DNA band was excised and DNA eluted using the Qiaquick protocol (Qiagen). The egfp fragment was digested with the restriction enzymes MluI and SacII and the digestion mixture was purified on a 0.8% agarose gel, the DNA band was excised and DNA eluted using the Qiaex protocol (Qiagen).

320 ng of the pLXPCMTV backbone and 80 ng of the MluI/SacII fragment were mixed and ligated for 14 h at 16° C. using T4 ligase (New England BioLabs). The ligase was inactivated at 65° C. for 20 min and the DNA butanol precipitated with 10 fold volume of butanol. The precipitated DNA was resuspended in water and electroporated into DH10B bacteria (Gibco). Ampicillin/Kanamycin resistant colonies were selected; DNA prepared and test digested with the restriction enzymes HpaI and sequenced. The final correct plasmid was designated pLXPCEGFP.r.

V. ReCon Expression Vector pRC1UbpshEGFP

1. Construction of the ReCon Expression Vector pRC1UbpshEGFP Containing the Inverse egfp Gene Within the 3'LTR and the Inverse Ubiquitin Promoter Within the 5'LTR The ReCon expression vector pRC1UbpshEGFP was constructed by ligation of the fragment containing the ubiquitin promoter obtained from plasmid pTEJ-8 (Johansen et al. (1990) FEBS Lett. 267:289–294) with the pLXPCEGFP.r backbone. For this purpose the ubiquitin promoter had to be first subcloned.

For subcloning the ubiquitin promoter the vector pLPCMTV had to be generated from pLXPCMTV by removing a XhoI/XhoI fragment containing the complete SV40neo cassette. The vector pLXPCMTV was digested with the restriction enzyme XhoI yielding a 2266 bp and a 5544 bp fragment.

The digestion mixture was purified on a 0.8% agarose gel and the 5544 bp fragment band was excised and the DNA eluted using the Qiaquick protocol (Qiagen).

20 ng of the 5544 bp backbone was religated for 14 h at 16° C. using T4 ligase (New England BioLabs). The ligase was inactivated at 65° C. for 20 min and the DNA butanol precipitated with 10 fold volume of butanol. The precipitated DNA was resuspended in water and electroporated into DH10B bacteria (Gibco). Ampicillin resistant colonies were selected, DNA prepared and test digested with the restriction enzymes SacII, EcoRI, ScaI and SpeI. The final correct intermediate plasmid was designated pLPCMTV.

The plasmid pTEJ-8 was digested with the restriction enzymes HindIII and NheI. The digestion mixture was purified on a 0.8% agarose gel. The 1586 bp fragment band was excised and the DNA eluted using the Qiaquick protocol (Qiagen). Nucleotides were filled in with the Klenow enzyme (Promega) for 30 min at 30° C. After inactivation of the Klenow enzyme for 30 min at 70° C. the 1590 bp fragment was purified by running on a 0.8% agarose gel, the DNA band was excised and the DNA eluted using the Qiaquick protocol (Qiagen).

The vector pLPCMTV was digested with the restriction enzyme PshAI and the digested DNA was dephosphorylated with alkaline phosphatase (Promega) for 60 min at 50° C. After inactivation of the phosphatase for 60 min at 65° C. the DNA was purified by running on a 0.8% agarose gel, the DNA band was excised and the DNA eluted using the Qiaquick protocol (Qiagen).

100 ng of the pLPCMTV backbone and 100 ng of the HindIII/NheI fragment were mixed and ligated for 14 h at 16° C. using T4 ligase (New England BioLabs). The ligase was inactivated at 65° C. for 20 min and the DNA butanol precipitated with 10 fold volume of butanol. The precipitated DNA was resuspended in water and electroporated into DH10B bacteria (Gibco). Ampicillin resistant colonies were selected, DNA prepared and test digested with the restriction enzymes StuI, AvrII, BgII and SacI. The final correct intermediate plasmid as designated pRC1psh.sub.

For cloning the ubiquitin promoter obtained from the plasmid pRC1psh.sub into the ProCon derived expression vector pLXPCEGFP.r, both plasmids were digested with the restriction enzymes SspI and BstEII yielding a 6044 bp backbone and 3103 bp fragment, respectively. The digestion mixtures were purified on a 0.8% agarose gel. The 6044 bp backbone fragment and the 3103 bp fragment bands were excised and the DNA eluted using the Qiaquick protocol (Qiagen).

100 ng of the pLXPCEGFP.r backbone and 75 ng of the 3103 bp fragment were mixed and ligated for 1 h at room temperature using T4 ligase (New England BioLabs). The ligase was inactivated at 65° C. for 20 min and the DNA butanol precipitated with 10 fold volume of butanol. The precipitated DNA was resuspended in water and electroporated into DH10B bacteria (Gibco). Ampicillin/Kanamycin resistant colonies were selected, DNA prepared and test digested with the restriction enzymes StuI and AvrII and sequenced. The final correct plasmid was designated pRC1UbpsKEGFP.

2. Production of Retroviral Particles Containing the egfp Gene and the Ubiquitin Promoter by Using the ReCon Expression Vector pRC1UbpshEGFP For transfection of packaging cell lines (PA317) $5 \times 10^5$ cells were seeded into 6-well dishes with a diameter of 35 mm. At the day of transfection 10 μg of pRC1UbpshEGFP was transfected using the calcium-phosphate protocol Cellfect Kit (Pharmacia) according to the manufacturer's instructions.

18 h post transfection the medium was changed and 24 h post transfection the medium containing the retroviral particles was removed and used for infection of target cells. 48 h post infection the ubiquitin/EGFP transfer was tested by FACS analysis of the target cells. New medium was added to the transfected packaging cells containing G418-Geneticin to select for stable transfected cell populations.

3. Infection of Target Cells with Retroviral Particles Resulting in egfp Gene Expression Regulated by the Ubiquitin Promoter After Reverse Transcription.

For infection of target cells (NIH/3T3) $5 \times 10^5$ cells in 10 ml medium were seeded in culture dishes with a diameter of 10 cm. At the day of infection, 2 ml of the supernatant containing vector virus (see above item 2) and 2 μl Polybrene (final concentration 8 μg/ml) were added to the cells and incubated. After 6 hours 8 ml of culture medium was added and 24 h later the EGFP expression tested by FACS analysis. New medium containing G418-Geneticin was added to the infected cells to select for stable infected cells.

VI. ReCon Expression Vector pRC2UbpacEGFP

1. Construction of the ReCon Expression Vector pRC2UbpacEGFP Containing the Inverse egfp Gene Within the 3'LTR and the Inverse Ubiquitin Promoter Between the R and U5 Region of the 5'LTR.

The vector pRC2pacEGFP was constructed by introducing a unique PacI restriction site between the R and U5 region within the 5'LTR of the expression vector pLXPCEGFP.r.

The PacI restriction site was introduced by using the PCR method. For the first PCR reaction (PCR 1) the left hand primer (5'-GGCGACACGGAAATGTTGAA-3') (SEQ ID NO:3) was specific to the U3 region and the right hand primer (5'-GCGGGTTAATTAATCGGATGCAAACAGCAAGAG-3') (SEQ ID NO:4) was specific to the beginning of the U5 region also creating the new PacI restriction site (underlined). The PCR resulted in a 936 bp fragment. For the second PCR reaction (PCR 2) the left hand primer (5'CATCC<u>TTAATTAA</u>GAATCGTGGTCTCGCTGTT-3') (SEQ ID NO:5) was specific to the beginning of the US region also creating the new PacI restriction site and the right hand primer (5'-GCCTGGTTGCTGACTAATTG-3') (SEQ ID NO:6) was specific to the end of the SV40ori. The PCR resulted in a 1095 bp fragment. The fragments from both PCR reactions were purified on a 0.8% agarose gel, the DNA bands were excised and DNA eluted using the Qiaquick protocol (Qiagen).

The vector pLXPCEGFP.r was digested with the restriction enzymes BamHI and SspI, the fragments from PCR 1 were digested with the restriction enzymes PacI and SspI, and the fragment from PCR 2 was digested with the restriction enzymes PacI and BamHI. The digestion mixtures were purified by running a 0.8% agarose gel, the DNA bands were excised and DNA eluted using the Qiaquick protocol (Qiagen).

25 ng of the pLXPCEGFP.r backbone, 100 ng of the PacI/SspI fragment of PCR 1 and 75 ng of the BamHI/PacI fragment of PCR 2 were mixed. For ligation the temperature was increased for 1° C. per hour from 10° C. to 21° C. and then incubated for 5 hours at 22° C. using T4 ligase (New England BioLabs). The ligase was inactivated at 65° C. for 20 min and the DNA transfected into DH5α bacteria (Gibco) using the $CaCl_2$ method. Ampicillin/Kanamycin resistant colonies were selected, DNA prepared and test digested with the restriction enzymes XmnI/StuI and XmnI/PacI and sequenced. The final correct intermediate plasmid was designated pRC2pacEGFP.

The ReCon expression vector pRC2UbpacEGFP was constructed by ligation of the fragment containing the ubiquitin promoter obtained from plasmid pTEJ-8(Johansen et al. (1990) FEBS Lett. 267:289–294) with the pRC2pacEGFP backbone.

The vector pRC2pacEGFP was digested with the restriction enzyme PacI linearising the vector, and the plasmid pTEJ-8 was digested with the restriction enzymes HindIII and NheI yielding a 1586 bp fragment. The digestion mixtures were purified by running a 0.8% agarose gel, the DNA bands were excised and DNA eluted using the Qiaquick protocol (Qiagen).

For blunt end ligation the overhanging nucleotide ends of the pRC2pacEGFP backbone were cut off with T4 polymerase (New England BioLabs) for 20 min at 12° C. After inactivation of the T4 polymerase for 10 min at 75° C. the DNA was purified by running on a 0.8% agarose gel, the DNA band was excised and DNA eluted using the Qiaquick protocol (Qiagen). Finally, the purified DNA was dephosphorylated for 60 min at 50° C. using the alkaline phosphatase (Promega), and the alkaline phosphatase inactivated for 60 min at 65° C.

The 1586 bp HindIII/NheI fragment was treated with the Klenow enzyme (New England BioLabs) to fill in nucleotides for blunt end ligation for 30 min at 30° C. After inactivation of the Klenow enzyme for 30 min at 70° C. the DNA was purified by running on a 0.8% agarose gel, the DNA band was excised and DNA eluted using the Qiaquick protocol (Qiagen).

175 ng of the pRC2pacEGFP backbone and 75 ng of the 1590 bp HindIII/NheI fragment were mixed and ligated for 14 h at 16° C. using T4 ligase (New England BioLabs). The ligase was inactivated at 65° C. for 20 min and the DNA butanol precipitated with 10 fold volume of butanol. The precipitated DNA was resuspended in water and electroporated into DH10B bacteria (Gibco). Ampicillin/Kanamycin resistant colonies were selected, DNA prepared and test digested with the restriction enzymes StuI, XhoI and AvrII and sequenced. The final correct plasmid was designated pRC2UbpacEGFP.

2. Production of Retroviral Particles Containing the egfp Gene and the Ubiquitin Promoter by Using the ReCon Expression Vector pRC2UbpacEGFP.

For transfection of packaging cell lines (PA317) 5×10$^5$ cells were seeded into 6-well dishes with a diameter of 35 mm. At the day of transfection 10 μg of pRC2UbpacEGFP was transfected using the calcium-phosphate protocol Cellfect Kit (Pharmacia) according to the manufacturer's instructions.

18 h post transfection the medium was changed, and 24 h post transfection the medium containing retroviral particles was removed and used for infection of target cells. 48 h post infection the ubiquitin/EGFP transfer was tested by FACS analysis of target cells. New medium containing G418-Geneticin was added to the transfected packaging cells to select for stable transfected cell populations.

3. Infection of Target Cells with Retroviral Particles Resulting in egfp Gene Expression Regulated by the Ubiquitin Promoter After Reverse Transcription For infection of target cells (NIH/3T3) 5×10$^5$ cells in 10 ml medium were seeded in culture dishes with a diameter of 10 cm. At the day of infection, 2 ml of the supernatant containing recombinant retroviral particles (see above item 2) and 2 μl Polybrene (final concentration 8 μg/ml) were added to the cells and incubated. After 6 hours, 8 ml of culture medium was added and 24 h later the EGFP expression tested by FACS analysis. The cells were diluted 1:50, 1:100 and 1:200 in culture medium and seeded in culture dishes. 12 h later new medium containing G418-Geneticin was added to select for infected cell clones.

VII. ReCon Expression Vector pRC2UbpacpmeEGFP

1. Construction of the ReCon Expression Vector pRC2UbpacpmeEGFP Containing the Inverse egfp Gene Within the 3'LTR and the Inverse Ubiquitin Promoter as Well as an Additional Unique PmeI Restriction Site for Easier Exchange of Promoters Between the R and U5 Region Within the 5'LTR The vector pRC2pacpmeEGFP was constructed by introducing a unique PmeI restriction site between the R and U5 region of the 5'LTR of the vector pRC2pacEGFP.

The PmeI restriction site was introduced by using the PCR method. For the first PCR reaction (PCR 1) the left hand primer (5'-GGCGACACGGAAATGTTGAA-3') (SEQ ID NO:3) was specific to the U3 region and the right hand primer (5'-GAGCTTT GTTTAAACCCAAGGAACAGCGAGACCAC-3') (SEQ ID NO:7) was specific to the center of the U5 region also creating the new PmeI restriction site (underlined). The PCR resulted in a 970 bp fragment. For the second PCR reaction (PCR 2) the left hand primer (5'-GAGCTTT GTTTAAACCCTTGGGAGGGTCTCCTCTG-3') (SEQ ID NO:8) was specific to the center of the U5 region also creating the new PmeI restriction site, and the right hand primer (5'-GCCTGGTTGCTGACTAATTG-3') (SEQ ID NO:6) was specific to the end of the SV40ori. The PCR resulted in a 1078 bp fragment. The fragments of both PCR reactions were purified on a 0.8% agarose gel, the DNA bands were excised and DNA eluted using the Qiaquick protocol (Qiagen).

The vector pRC2pacEGFP was digested with the restriction enzymes BamHI and SspI resulting in a 5711 bp fragment, the fragment from PCR 1 was digested with the restriction enzymes PmeI and SspI and the fragment from PCR 2 was digested with the restriction enzymes PmeI and BamHI. The digestion mixtures were purified by running a 0.8% agarose gel, the DNA bands were excised and DNA eluted using the Qiaquick protocol (Qiagen).

25 ng of the pRC2pacEGFP backbone, 100 ng of the PmeI/SspI fragment of PCR 1 and 75 ng of the BamHI/PmeI fragment of PCR 2 were mixed. For ligation the temperature was increased for 1° C. per hour from 10° C. to 21° C. and then incubated for 5 hours at 22° C. using T4 ligase (New England BioLabs). The ligase was inactivated at 65° C. for 20 min and the DNA transfected into DH5α bacteria (Gibco) using the CaCl$_2$ method. Ampicillin/Kanamycin resistant colonies were selected, DNA prepared and test digested with the restriction enzymes XmuI/StuI and XmuI/PmeI and sequenced. The final correct intermediate plasmid was designated pRC2pacpmeEGFP.

The ReCon expression vector pRC2UbpacpmeEGFP was constructed by ligation of the fragment containing the ubiquitin promoter obtained by the PCR method from pTEJ-8 (Johansen et al. (1990) FEBS Lett. 267:289–294) with the pRC2pacpmeEGFP backbone.

For the PCR reaction the left hand primer (5'-GAGCCTT GTTTAAACGAGCTCGCGAAAGCTAGC-3') (SEQ ID NO:9) was specific to the beginning of the ubiquitin promoter gene also creating a PmeI restriction site (underlined) and the right hand primer (5'-GCGG TTAATTAACGTCGACCTGCAGCCAAGCT-3') (SEQ ID NO:10) was specific to the end of the ubiquitin promoter gene also creating a PacI restriction site (underlined). PCR resulted in a 1647 bp fragment. The fragment was purified on a 0.8% agarose gel, the DNA band was excised and DNA eluted using the Qiaquick protocol (Qiagen). The PCR fragment was digested with the restriction enzymes PacI and PmeI yielding a 1628 bp fragment. The digestion mixture was purified on a 0.8% agarose gel, the DNA band was excised and DNA eluted using the Qiaquick protocol (Qiagen).

The pRC2pacpmeEGFP backbone was digested with the restriction enzymes PacI and PmeI yielding a 7549 bp fragment. The digestion mixture was purified on a 0.8% agarose gel, the DNA band was excised and DNA eluted using the Qiaquick protocol (Qiagen).

25 ng of the pRC2pacpmeEGFP backbone and 100 ng of the PacI/PmeI fragment were mixed and ligated for 14 h at 16° C. using T4 ligase (New England BioLabs). The ligase was inactivated at 65° C. for 20 min and the DNA butanol precipitated with 10 fold volume of butanol. The precipitated DNA was resuspended in water and electroporated into DH10B bacteria (Gibco). Ampicillin/Kanamycin resistant colonies were selected, DNA prepared and test digested with the restriction enzymes StuI, HindIII and AvrII and sequenced. The final correct plasmid was designated pRC2UbpacpmeEGFP.

2. Production of Retroviral Particles Containing the egfp Gene and the Ubiquitin Promoter by Using the ReCon Expression Vector pRC2UbpacpmeEGFP For transfection of packaging cell lines (PA317) 5×10$^5$ cells were seeded into 6-well dishes with a diameter of 35 mm. At the day of transfection 10 μg of pRC2UbpacpmeEGFP was transfected using the calcium-phosphate protocol Cellfect Kit (Pharmacia) according to the manufacturer's instructions.

18 h post transfection the medium was changed, and 24 h post transfection the medium containing retroviral particles was removed and used for infection of target cells. 48 h post infection the ubiquitin/EGFP transfer was tested by FACS analysis of target cells. New medium containing G418-Geneticin was added to the transfected packaging cells to select for stable transfected cell populations.

3. Infection of Target Cells with Retroviral Particles Resulting in the egfp Gene Expression Regulated by the Ubiquitin Promoter After Reverse Transcription For infection of target cells (NIH/3T3) $5\times10^5$ cells in 10 ml medium were seeded in culture dishes with a diameter of 10 cm. At the day of infection, 2 ml of the supernatant containing recombinant retroviral particles (see above item 2) and 2 μl Polybrene (final concentration 8 μg/ml) were added to the cells and incubated. After 6 hours, 8 ml of culture medium was added and 24 h later the EGFP expression tested by FACS analysis, Cells were diluted 1:50, 1:1100 and 1:200 in culture medium and seeded in culture dishes. 12 h later medium containing G418-Geneticin was added to the infected cells to select for stable infected cell clones.

While this invention has been particularly shown and described with references to preferred embodiments thereof, it will be understood by those skilled in the art that various changes in form and details may be made therein without departing from the scope of the invention encompassed by the appended claims.

What is claimed is:

1. A retroviral vector comprising one or more promoters inserted in antisense orientation within the 5' long terminal repeat (LTR) region and one or more coding sequences inserted in antisense orientation within the 3' LTR region, both the promoter as well as the coding sequence inserted in such a way as to ensure that the promoter and the coding sequence become duplicated during the process of reverse transcription in a target cell and appear in the 3' as well as the 5' LTR region of the resulting provirus in a fashion where the promoter is located upstream of the coding sequence and drives expression of the coding sequence.

2. The retroviral vector according to claim 1, wherein said one or more promoters is inserted within the U5 region of the 5' LTR.

3. The retroviral vector according to claim 1, wherein said one or more coding sequences is inserted within the U3 region of the 3' LTR.

4. The retroviral vector according to claim 1, wherein said one or more promoters is a constitutive promoter.

5. The retroviral vector according to claim 1, wherein said retroviral vector is based on a promoter conversion vector.

6. The retroviral vector according to claim 1, wherein said one or more coding sequences comprises DNA which is heterologous to the vector.

7. The retroviral vector according to claim 6, wherein said one or more coding sequences is selected from one or more elements of the group consisting of marker genes, therapeutic genes, antiviral genes, antitumour genes, cytokine genes, toxin genes and combinations thereof.

8. The retroviral vector according to claim 1, wherein said retroviral vector is replication-defective.

9. The retroviral vector according to claim 8, wherein said retroviral vector is based on a vector of the pLXSN family.

10. A recombinant retroviral vector system comprising:
 a) a retroviral vector comprising one or more promoters inserted in antisense orientation within the 5' long terminal repeat (LTR) region and one or more coding sequences inserted in antisense orientation within the 3' LTR region, both the promoter as well as the coding sequence inserted in such a way as to ensure that the promoter and the coding sequence become duplicated during the process of reverse transcription in a target cell and appear in the 3' as well as in the 5' LTR region of the resulting provirus in a fashion where the promoter is located upstream of the coding sequence and drives expression of the coding sequence, and
 b) a packaging cell line harbouring at least one retroviral construct coding for proteins required for said retroviral vector to be packaged.

11. A retroviral particle produced by transfecting a packaging cell line of a retroviral vector system with a retroviral vector comprising one or more promoters inserted in antisense orientation within the 5' long terminal repeat (LTR) region and one or more coding sequences inserted in antisense orientation within the 3' LTR region, both the promoter as well as the coding sequence inserted in such a way as to ensure that the promoter and the coding sequence become duplicated during the process of reverse transcription in a target cell and appear in the 3' as well as in the 5' LTR region of the resulting provirus in a fashion where the promoter is located upstream of the coding sequence and drives expression of the coding sequence, and isolating the resulting retroviral particle.

12. A recombinant retroviral provirus produced by the infection of target cells with a recombinant retroviral particle according to claim 11.

13. A host cell infected with a retroviral particle according to claim 11.

14. A retroviral vector comprising one or more promoters inserted in antisense orientation within the U5 region of the 5' long terminal repeat (LTR) region and one or more coding sequences inserted in antisense orientation within the U3 region of the 3' LTR region, both the promoter as well as the coding sequence inserted in such a way as to ensure that the promoter and the coding sequence become duplicated during the process of reverse transcription in a target cell and appear in the 3' as well as in the 5' LTR region of the resulting provirus in a fashion wherein the promoter is located upstream of the coding sequence and drives expression of the coding sequence.

15. The retroviral vector according to claim 14, wherein said one or more coding sequences comprises DNA which is heterologous to the vector.

16. The retroviral vector according to claim 15, wherein said one or more coding sequences is selected from one or more elements of the group consisting of marker genes, antiviral genes, antitumour genes, cytokine genes, toxin genes and combinations thereof.

* * * * *

SEQUENCE LISTING

<160> NUMBER OF SEQ ID NOS: 10

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
atagtaacgc gtggtcgcca ccatggtgag                              30

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
gcgatccgcg gtggacaaac cacaactaga                              30

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ggcgacacgg aaatgttgaa                                         20

<210> SEQ ID NO 4
<211> LENGTH: 33
<212> TYPE: DNA
<213> ORGANISM: Artificial Sequence
<220> FEATURE:
<223> OTHER INFORMATION: Primer

<400> SEQUENCE: 4
gcgggttaat taatcggatg caaacagcaa gag                          33

<210> SEQ ID NO 5
<211> LENGTH: 32
<212> TYPE: DNA
<213> ORGANISM: Artificial Sequence
<220> FEATURE:
<223> OTHER INFORMATION: Primer

<400> SEQUENCE: 5

-continued

```
catccttaat taagaatcgt ggtctcgctg tt                            32

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gcctggttgc tgactaattg                                          20

<210> SEQ ID NO 7
<211> LENGTH: 35
<212> TYPE: DNA
<213> ORGANISM: Artificial Sequence
<220> FEATURE:
<223> OTHER INFORMATION: Primer

<400> SEQUENCE: 7
gagctttgtt taaacccaag gaacagcgag accac                         35

<210> SEQ ID NO 8
<211> LENGTH: 35
<212> TYPE: DNA
<213> ORGANISM: Artificial Sequence
<220> FEATURE:
<223> OTHER INFORMATION: Primer

<400> SEQUENCE: 8
gagctttgtt taaacccttg ggagggtctc ctctg                         35

<210> SEQ ID NO 9
<211> LENGTH: 33
<212> TYPE: DNA
<213> ORGANISM: Artificial Sequence
<220> FEATURE:
<223> OTHER INFORMATION: Primer

<400> SEQUENCE: 9
gagccttgtt taaacgagct cgcgaaagct agc                           33

<210> SEQ ID NO 10
<211> LENGTH: 32
<212> TYPE: DNA
<213> ORGANISM: Artificial Sequence
<220> FEATURE:
<223> OTHER INFORMATION: Primer

<400> SEQUENCE: 10
gcggttaatt aacgtcgacc tgcagccaag ct                            32
```